(12) United States Patent
Dozeman

(10) Patent No.: US 11,844,495 B2
(45) Date of Patent: Dec. 19, 2023

(54) TECHNIQUES FOR DETECTING ERRORS OR LOSS OF ACCURACY IN A SURGICAL ROBOTIC SYSTEM

(71) Applicant: MAKO Surgical Corp., Weston, FL (US)

(72) Inventor: Michael Dale Dozeman, Portage, MI (US)

(73) Assignee: MAKO Surgical Corp., Weston, FL (US)

( * ) Notice: Subject to any disclaimer, the term of this patent is extended or adjusted under 35 U.S.C. 154(b) by 0 days.

(21) Appl. No.: 18/095,550

(22) Filed: Jan. 11, 2023

(65) Prior Publication Data

US 2023/0165647 A1 Jun. 1, 2023

Related U.S. Application Data

(63) Continuation of application No. 17/328,221, filed on May 24, 2021, now Pat. No. 11,602,401, which is a
(Continued)

(51) Int. Cl.
*A61B 34/00* (2016.01)
*A61B 34/30* (2016.01)
(Continued)

(52) U.S. Cl.
CPC ............. *A61B 34/30* (2016.02); *B25J 9/1674* (2013.01); *B25J 9/1694* (2013.01);
(Continued)

(58) Field of Classification Search
CPC ............ A61B 34/30; A61B 2034/2048; A61B 2034/2059; A61B 2034/2072; B25J 9/1674; B25J 9/1694; G05B 2219/45117; G05B 2219/39391; G05B 2219/45123; G05B 2219/37288
See application file for complete search history.

(56) References Cited

U.S. PATENT DOCUMENTS 5,913,820 A 6/1999 Bladen et al.
7,086,293 B2 8/2006 Heiligensetzer et al.
(Continued)

OTHER PUBLICATIONS

International Search Report for Application No. PCT/US2017/066083 dated Mar. 23, 2018, 3 pages.

*Primary Examiner* — Ian Jen
(74) *Attorney, Agent, or Firm* — Howard & Howard Attorneys PLLC

(57) ABSTRACT

Systems and methods for detecting an error in a surgical system. The surgical system includes a manipulator with a base and a plurality of links and the manipulator supports a surgical tool. The system includes a navigation system with a tracker and a localizer to monitor a state of the tracker. Controller(s) determine values of a first transform between a state of the base of the manipulator and a state of one or both of the localizer and the tracker of the navigation system. The controller(s) determine values of a second transform between the state of the localizer and the state of the tracker. The controller(s) combine values of the first transform and the second transform to determine whether an error has occurred relating to one or both of the manipulator and the localizer.

20 Claims, 5 Drawing Sheets

Related U.S. Application Data continuation of application No. 16/848,204, filed on Apr. 14, 2020, now Pat. No. 11,033,343, which is a continuation of application No. 15/840,258, filed on Dec. 13, 2017, now Pat. No. 10,660,715.

(60) Provisional application No. 62/435,258, filed on Dec. 16, 2016.

(51) Int. Cl.
*B25J 9/16* (2006.01)
*A61B 34/20* (2016.01)

(52) U.S. Cl.
CPC ............. *A61B 2034/2046* (2016.02); *A61B 2034/2048* (2016.02); *A61B 2034/2059* (2016.02); *A61B 2034/2072* (2016.02); *G05B 2219/37288* (2013.01); *G05B 2219/39391* (2013.01); *G05B 2219/45117* (2013.01); *G05B 2219/45123* (2013.01)

(56) References Cited

U.S. PATENT DOCUMENTS

| | | | |
|---|---|---|---|
| 7,155,315 B2 | 12/2006 | Niemeyer et al. | |
| 7,272,467 B2 | 9/2007 | Goncalves et al. | |
| 7,689,321 B2 | 3/2010 | Karlsson | |
| 7,806,891 B2 | 10/2010 | Nowlin et al. | |
| 8,073,528 B2 | 12/2011 | Zhao et al. | |
| 8,108,072 B2 | 1/2012 | Zhao et al. | |
| 8,398,541 B2 | 3/2013 | DiMaio et al. | |
| 8,939,982 B2 | 1/2015 | Chellaoui | |
| 8,971,597 B2 | 3/2015 | Zhao et al. | |
| 9,008,757 B2 | 4/2015 | Wu | |
| 9,060,794 B2 | 6/2015 | Kang et al. | |
| 9,102,055 B1 | 8/2015 | Konolige et al. | |
| 9,119,655 B2 | 9/2015 | Bowling et al. | |
| 9,125,690 B2 | 9/2015 | Wohlgemuth | |
| 9,205,560 B1 | 12/2015 | Edsinger et al. | |
| 9,238,304 B1 | 1/2016 | Bradski et al. | |
| 9,259,282 B2 | 2/2016 | Azizian et al. | |
| 10,555,775 B2 | 2/2020 | Hoffman et al. | |
| 10,660,715 B2 | 5/2020 | Dozeman | |
| 10,792,107 B2 | 10/2020 | Hoffman et al. | |
| 11,033,343 B2 | 6/2021 | Dozeman | |
| 2012/0030429 A1* | 2/2012 | Synge | G06F 16/24552 711/E12.024 |
| 2014/0276949 A1 | 9/2014 | Staunton et al. | |
| 2015/0051733 A1 | 2/2015 | Nowlin et al. | |
| 2020/0237457 A1 | 7/2020 | Dozeman | |
| 2021/0275261 A1 | 9/2021 | Dozeman | |

\* cited by examiner

TECHNIQUES FOR DETECTING ERRORS OR LOSS OF ACCURACY IN A SURGICAL ROBOTIC SYSTEM

CROSS-REFERENCE TO RELATED APPLICATIONS

The subject application is a continuation of U.S. patent application Ser. No. 17/328,221, filed May 24, 2021, which is a continuation of U.S. patent application Ser. No. 16/848,204, filed Apr. 14, 2020, now U.S. Pat. No. 11,033,343, which is a continuation of U.S. patent application Ser. No. 15/840,258, filed Dec. 13, 2017, now U.S. Pat. No. 10,660,715, which claims priority to and all the benefits of U.S. Provisional Patent App. No. 62/435,258, filed on Dec. 16, 2016, the contents of each of the aforementioned applications being hereby incorporated by reference in their entirety.

TECHNICAL FIELD

The present disclosure relates generally to techniques for detecting errors or loss of accuracy in a surgical robotic system.

BACKGROUND

Robotic systems are commonly used to perform surgical procedures and typically include a robot comprising a robotic arm and a tool coupled to an end of the robotic arm for engaging a surgical site. Often, a tracking system, such as optical localization, is utilized to track positioning of the robot and the surgical site. Kinematic data from the robot may be aggregated with data from the tracking system to update positioning of the robot or for redundant position detection. Tracking systems often track the robot at much higher speeds than the robot can respond. This high speed tracking data is often unsuitable to be utilized directly by the robot, due to both noise and control system stability issues. In many cases, low-pass filtering is used to reduce the noise levels, which improves the signal-to-noise ratio of the commands given to the robot and results in smoother movement and improved performance of the robot arm. In addition, since the tracking system measurement of the tool is part of an outer positioning loop, it is important to not close this outer loop at a higher bandwidth than the robot is capable of responding. The aforementioned low-pass filter also serves this purpose as a control system compensator, effectively lowering the bandwidth of the outer loop to that needed to ensure stable performance. As a result, updating position of the robot based on data from the tracking system has delays due to the filtering of the data.

Although such systems may update the steady state positioning or detect static positioning errors using this technique, such systems are not equipped to determine whether errors or loss of system accuracy has occurred in the system in real time. Instead, such techniques detect errors only after data from the tracking system is filtered or compensated based on control needs of the robot. In other words, any detection of errors in such systems is delayed. Such delay in detecting errors may result in damage to the system or the surgical site, even if such delay is merely hundreds of milliseconds.

As such, there is a need in the art for systems and methods for addressing at least the aforementioned problems.

SUMMARY

According to a first aspect, surgical system is provided, comprising: a surgical tool; a manipulator comprising a base and a plurality of links and being configured to support the surgical tool; a navigation system comprising a tracker and a localizer being configured to monitor a state of the tracker; and one or more controllers coupled to the manipulator and the navigation system and being configured to: determine values of a first transform between a state of the base of the manipulator and a state of one or both of the localizer and the tracker of the navigation system; determine values of a second transform between the state of the localizer and the state of the tracker; and combine values of the first transform and the second transform to determine whether an error has occurred relating to one or both of the manipulator and the localizer.

According to a second aspect, a method is provided of operating a surgical system comprising a surgical tool, a manipulator comprising a base and a plurality of links and being configured to support the surgical tool, a navigation system comprising a tracker and a localizer being configured to monitor a state of the tracker, one or more controllers coupled to the manipulator and the navigation system, the method comprising the one or more controllers performing the following: determining values of a first transform between a state of the base of the manipulator and a state of one or both of the localizer and the tracker of the navigation system; determining values of a second transform between the state of the localizer and the state of the tracker; combining values of the first transform and the second transform for determining whether an error has occurred relating to one or both of the manipulator and the localizer, wherein the error is defined as one or more of: undesired movement of the manipulator; undesired movement of the localizer; failure of any one or more components of the manipulator or the localizer; and improper calibration data.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. Overview

Referring to the Figures, wherein like numerals indicate like or corresponding parts throughout the several views, a robotic surgical system 10 (hereinafter "system") and method for operating the system 10 and detecting errors or loss in accuracy of the system 10 are shown throughout.

Figure 1:
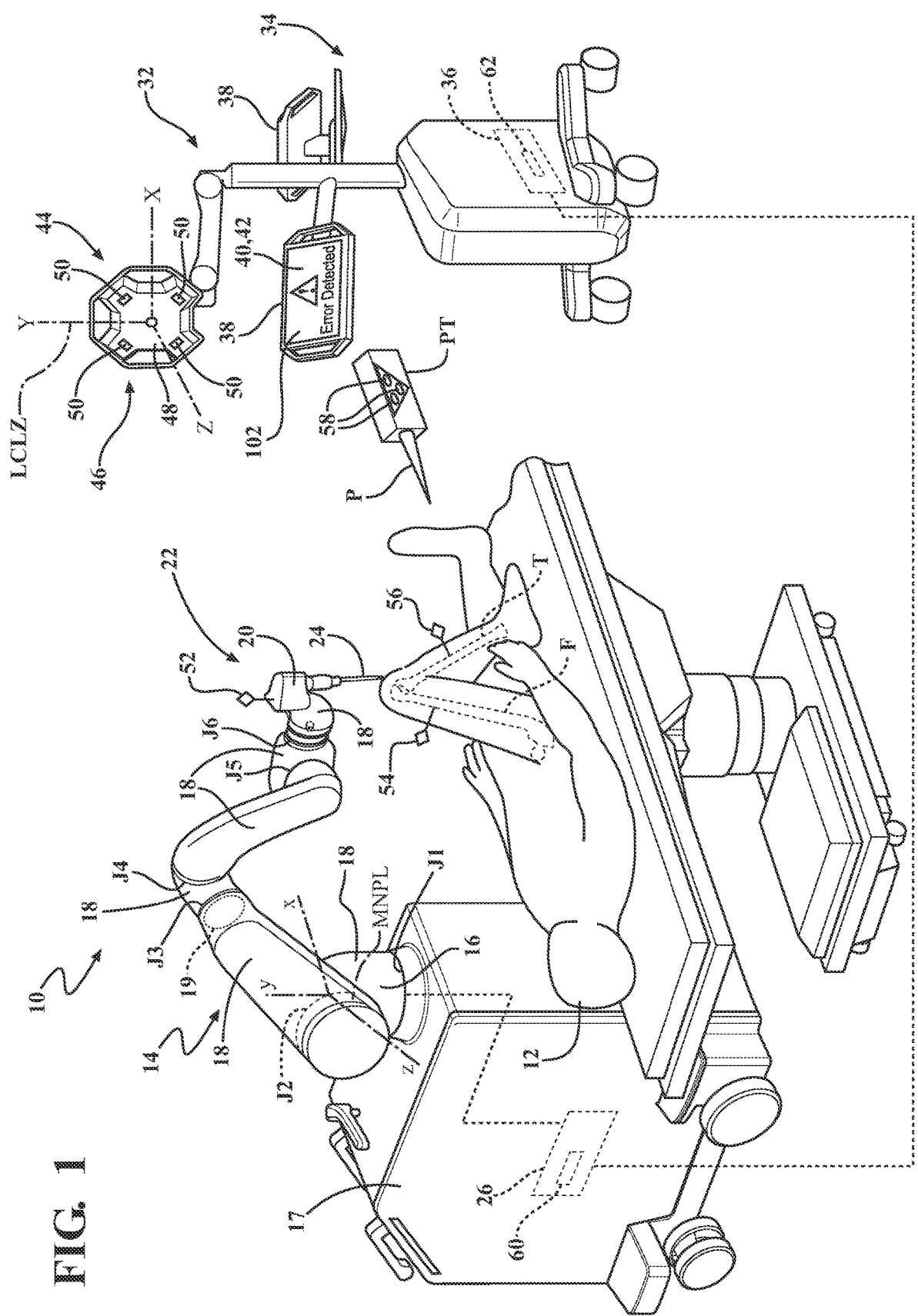
FIG. 1 is a perspective view of a robotic surgical system for treating an anatomy of a patient with a tool, according to one embodiment of the invention.

As shown in FIG. 1, the system 10 is a robotic surgical system for treating an anatomy of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some embodiments, the surgical procedure involves partial or total knee or hip replacement surgery. In one embodiment, the system 10 is designed to cut away material to be replaced by surgical implants such as hip and knee implants, including unicompartmental, bicompartmental, multicompartmental, or total knee implants. Some of these types of implants are shown in U.S. Patent Application Publication No. 2012/0330429, entitled, "Prosthetic Implant and Method of Implantation," the disclosure of which is hereby incorporated by reference. Those skilled in the art appreciate that the system 10 and method disclosed herein may be used to perform other procedures, surgical or non-surgical, or may be used in industrial applications or other applications where robotic systems are utilized.

The system 10 includes a manipulator 14. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1) or a parallel arm configuration. In other embodiments, more than one manipulator 14 may be utilized in a multiple arm configuration. The manipulator 14 comprises a plurality of joints (J) and a plurality of joint encoders 19 located at the joints (J) for determining position data of the joints (J). For simplicity, only one joint encoder 19 is illustrated in FIG. 1, although it is to be appreciated that the other joint encoders 19 may be similarly illustrated. The manipulator 14 according to one embodiment has six joints (J1-J6) implementing at least six-degrees of freedom (DOF) for the manipulator 14. However, the manipulator 14 may have any number of degrees of freedom and may have any suitable number of joints (J) and redundant joints (J).

The base 16 of the manipulator 14 is generally a portion of the manipulator 14 that is stationary during usage thereby providing a fixed reference coordinate system (i.e., a virtual zero pose) for other components of the manipulator 14 or the system 10 in general. Generally, the origin of the manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In a preferred embodiment, the base 16 is defined at an intersection of the axes of joints J1 and J2 (see FIG. 3). Thus, although joints J1 and J2 are moving components in reality, the intersection of the axes of joints J1 and J2 is nevertheless a virtual fixed reference point which does not move in the manipulator coordinate system MNPL.

A surgical tool 20 (hereinafter "tool") couples to the manipulator 14 and is movable relative to the base 16 to interact with the anatomy in certain modes. The tool 20 is or forms part of an end effector 22. The tool 20 may be grasped by the operator in certain modes. One exemplary arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference. The tool 20 includes an energy applicator 24 designed to contact the tissue of the patient 12 at the surgical site. The energy applicator 24 may be a drill, a saw blade, a bur, an ultrasonic vibrating tip, or the like. The manipulator 14 and/or manipulator cart 17 house a manipulator computer 26, or other type of control unit. The tool 20 comprises a TCP, which in one embodiment, is a predetermined reference point defined at the energy applicator 24. The TCP has known position in its own coordinate system. In one embodiment, the TCP is assumed to be located at the center of a spherical feature of the tool 20 such that only one point is tracked. The TCP may relate to a bur having a specified diameter.

Figure 2:
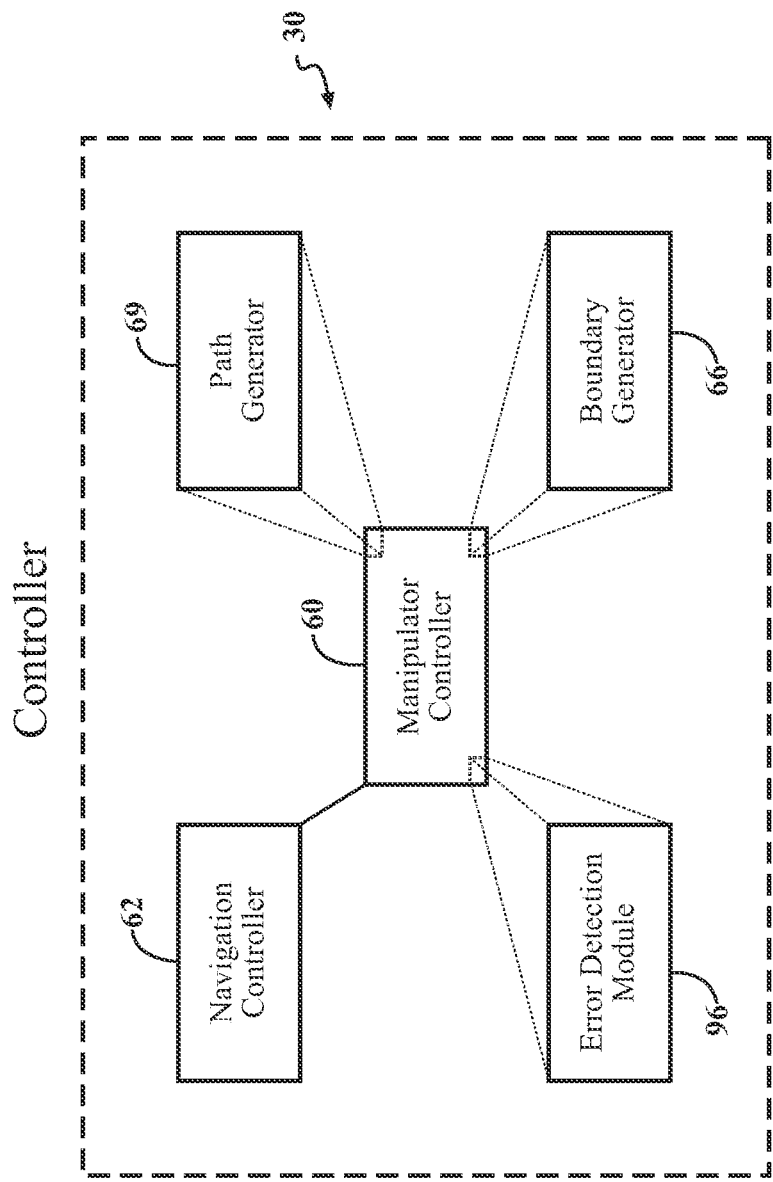
FIG. 2 is a block diagram of a controller for controlling the robotic surgical system and for detecting errors or loss in accuracy of the same, according to one embodiment of the invention.

Referring to FIG. 2, the system 10 includes a controller 30. The controller 30 includes software and/or hardware for controlling the manipulator 14. The controller 30 directs the motion of the manipulator 14 and controls a state (position and/or orientation) of the tool 20 with respect to a coordinate system. In one embodiment, the coordinate system is a manipulator coordinate system MNPL, as shown in FIG. 1. The manipulator coordinate system MNPL has an origin located at any suitable pose with respect to the manipulator 14. Axes of the manipulator coordinate system MNPL may be arbitrarily chosen as well. Generally, the origin of the manipulator coordinate system MNPL is defined at the fixed reference point of the base 16. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference.

As shown in FIG. 1, the system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformation techniques described herein.

The navigation system 32 includes a cart assembly 34 that houses a navigation computer 36, and/or other types of control units. A navigation interface is in operative communication with the navigation computer 36. The navigation interface includes one or more displays 38. The navigation system 32 is capable of displaying a graphical representation of the relative states of the tracked objects to the operator using the one or more displays 38. First and second input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof.

The navigation system 32 also includes a navigation localizer 44 (hereinafter "localizer") that communicates with the navigation computer 36. In one embodiment, the localizer 44 is an optical localizer and includes a camera unit 46. The camera unit 46 has an outer casing 48 that houses one or more optical sensors 50.

The navigation system 32 includes one or more trackers. In one embodiment, the trackers include a pointer tracker PT, a tool tracker 52, a first patient tracker 54, and a second patient tracker 56. In the illustrated embodiment of FIG. 1, the tool tracker 52 is firmly attached to the tool 20, the first patient tracker 54 is firmly affixed to the femur F of the patient 12, and the second patient tracker 56 is firmly affixed to the tibia T of the patient 12. In this embodiment, the patient trackers 54, 56 are firmly affixed to sections of bone. The pointer tracker PT is firmly affixed to a pointer P used for registering the anatomy to the localizer coordinate system LCLZ. Those skilled in the art appreciate that the trackers 52, 54, 56, PT may be fixed to their respective components in any suitable manner Additionally, the navigation system 32 may include trackers for other components of the system, including, but not limited to, the base 16, the cart 17, and any one or more links 18 of the manipulator 14.

Any one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of each of the trackers 52, 54, 56, which correspond respectively to the state of the tool 20, the femur (F) and the tibia (T). The localizer 44 provides the state of the trackers 52, 54, 56 to the navigation computer 36. In one embodiment, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one embodiment of the navigation system 32 is shown in the Figures, the navigation system 32 may have any other suitable configuration for tracking the tool 20 and the patient 12. In one embodiment, the navigation system 32 and/or localizer 44 are ultrasound-based. For example, the navigation system 32 may comprise an ultrasound imaging device coupled to the navigation computer 36. The ultrasound imaging device images any of the aforementioned objects, e.g., the tool 20 and the patient 12 and generates state signals to the controller 30 based on the ultrasound images. The ultrasound images may be 2-D, 3-D, or a combination of both. The navigation computer 36 may process the images in near real-time to determine states of the objects. The ultrasound imaging device may have any suitable configuration and may be different than the camera unit 46 as shown in FIG. 1.

In another embodiment, the navigation system 32 and/or localizer 44 are radio frequency (RF)-based. For example, the navigation system 32 may comprise an RF transceiver in communication with the navigation computer 36. Any of the tool 20 and the patient 12 may comprise RF emitters or transponders attached thereto. The RF emitters or transponders may be passive or actively energized. The RF transceiver transmits an RF tracking signal and generates state signals to the controller 30 based on RF signals received from the RF emitters. The navigation computer 36 and/or the controller 30 may analyze the received RF signals to associate relative states thereto. The RF signals may be of any suitable frequency. The RF transceiver may be positioned at any suitable location to effectively track the objects using RF signals. Furthermore, the RF emitters or transponders may have any suitable structural configuration that may be much different than the trackers 52, 54, 56 as shown in FIG. 1.

In yet another embodiment, the navigation system 32 and/or localizer 44 are electromagnetically based. For example, the navigation system 32 may comprise an EM transceiver coupled to the navigation computer 36. The tool 20 and the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the controller 30 based upon EM signals received from the trackers. The navigation computer 36 and/or the controller 30 may analyze the received EM signals to associate relative states thereto. Again, such navigation system 32 embodiments may have structural configurations that are different than the navigation system 32 configuration as shown throughout the Figures.

Those skilled in the art appreciate that the navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other embodiments of the navigation system 32 described herein. For example, the navigation system 32 may utilize solely inertial tracking or any combination of tracking techniques.

As shown in FIG. 2, the controller 30 further includes software modules. The software modules may be part of a computer program or programs that operate on the manipulator computer 26, navigation computer 36, or a combination thereof, to process data to assist with control of the system 10. The software modules include instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the manipulator 14. In one embodiment, as shown in FIG. 1, the manipulator controller 60 is implemented on the manipulator computer 26. The manipulator controller 60 may receive and process data from a single source or multiple sources. The controller 30 further includes a navigation controller 62 for communicating the state data relating to the femur F, tibia T, and tool 20 to the manipulator controller 60. The manipulator controller 60 receives and processes the state data provided by the navigation controller 62 to direct movement of the manipulator 14. In one embodiment, as shown in FIG. 1, the navigation controller 62 is implemented on the navigation computer 36. The manipulator controller 60 or navigation controller 62 may also communicate states of the patient 12 and tool 20 to the operator by displaying an image of the femur F and/or tibia T and the tool 20 on the one or more displays 38. The manipulator computer 26 or navigation computer 36 may also command display of instructions or request information using the display 38 to interact with the operator and for directing the manipulator 14.

Figure 3:
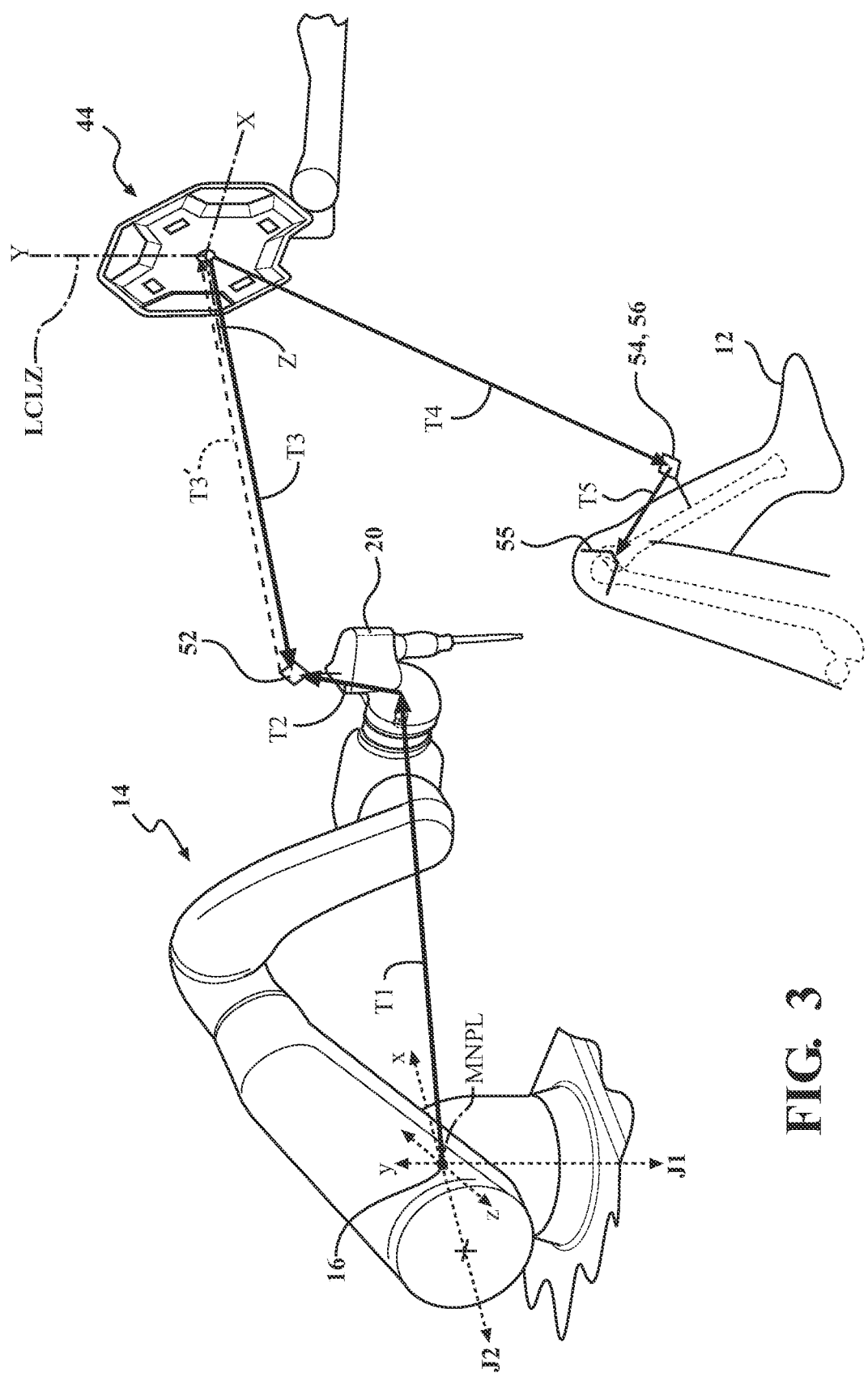
FIG. 3 is a perspective view illustrating transforms between a manipulator and a navigation system of the robotic surgical system, according to one embodiment of the invention.

As shown in FIG. 2, the controller 30 includes a boundary generator 66. The boundary generator 66 is a software module that may be implemented on the manipulator controller 60, as shown in FIG. 2. Alternatively, the boundary generator 66 may be implemented on other components, such as the navigation controller 62. The boundary generator 66 generates virtual boundaries 55 for constraining the tool 20, as shown in FIG. 3. Such virtual boundaries 55 may also be referred to as virtual meshes, virtual constraints, or the like. The virtual boundaries 55 may be defined with respect to a 3-D bone model registered to the one or more patient trackers 54, 56 such that the virtual boundaries 55 are fixed relative to the bone model. The state of the tool 20 is tracked relative to the virtual boundaries 55. In one embodiment, the state of the TCP of the tool 20 is measured relative to the virtual boundaries 55 for purposes of determining when and where haptic feedback force is applied to the manipulator 14, or more specifically, the tool 20.

A tool path generator 68 is another software module run by the controller 30, and more specifically, the manipulator controller 60. The tool path generator 68 generates a path for the tool 20 to traverse, such as for removing sections of the anatomy to receive an implant. One exemplary system and method for generating the tool path is explained in U.S. Pat. No. 9,119,655, entitled, "Surgical Manipulator Capable of Controlling a Surgical Instrument in Multiple Modes," the disclosure of which is hereby incorporated by reference. In some embodiments, the virtual boundaries 55 and/or tool paths may be generated offline rather than on the manipulator computer 26 or navigation computer 36. Thereafter, the virtual boundaries 55 and/or tool paths may be utilized at runtime by the manipulator controller 60. Yet another software module in FIG. 2 is an error detection module 96, the details of which are described below.

II. Data Fusion and Filtering

As described above, the manipulator 14 and the navigation system 32 operate with respect to different coordinate systems, i.e., the manipulator coordinate system MNPL and the localizer coordinate system LCLZ, respectively. As such, in some embodiments, the controller 30 fuses data from the manipulator 14 and the navigation system 32 for controlling the manipulator 14 using the navigation system 32. To do so, the controller 30 utilizes data fusion techniques as described herein.

In general, the controller 30 acquires raw data of various transforms between components of the system 10. The controller 30 combines and filters this raw data, and creates a filtered relationship between the base 16 of the manipulator 14 and the localizer 44, and ultimately produces a filtered relationship between the base 16 and one or more of the patient trackers 54, 56 based on the filtered data to control the manipulator 14.

As used herein, the term "raw" is used to describe data representing an actual or true state of one or more components of the system 10 (e.g., base 16, tool 20, localizer 44, trackers 52, 54, 56) relative to at least another component(s) of the system 10, whereby the raw data is obtained instantaneously (in practically real time) from its respective source such that the raw data is unfiltered. The raw data is an unaltered or minimally processed measurement.

As used herein, the term "filtered" is used to describe raw data that is filtered according to a filter length and that represents a filtered state of one or more components of the system 10 relative to at least another component(s) of the system 10. The filtered data is delayed with respect to the instantaneously obtained raw data due to application of the filter length in the filter. As will be described below, the raw data is ultimately filtered to control the manipulator 14. Additional details related to filtering are described below.

Each tracked component has its own coordinate system separate from the manipulator coordinate system MNPL and localizer coordinate system LCLZ. The state of each component is defined by its own coordinate system with respect to MNPL and/or LCLZ. Each of these coordinate systems has an origin that may be identified as a point relative to the origin of the manipulator coordinate system MNPL and/or the localizer coordinate system LCLZ. A vector defines the position of the origin of each of these coordinate systems relative to another one of the other coordinate systems. The location of a coordinate system is thus understood to be the location of the origin of the coordinate system. Each of these coordinate systems also has an orientation that, more often than not, is different from the coordinate systems of the other components. The orientation of a coordinate system may be considered as the relationship of the X, Y and Z-axes of the coordinate system relative to the corresponding axes of another coordinate system, such as MNPL and/or LCLZ.

The state of one component of the system 10 relative to the state of another component is represented as a transform (T). In one embodiment, each transform (T) is specified as a transformation matrix, such as a 4×4 homogenous transformation matrix. The transformation matrix, for example, includes three unit vectors representing orientation, specifying the axes (X, Y, Z) from the first coordinate system expressed in coordinates of the second coordinate system (forming a rotation matrix), and one vector (position vector) representing position using the origin from the first coordinate system expressed in coordinates of the second coordinate system.

The transform (T), when calculated, gives the state (position and/or orientation) of the component from the first coordinate system given with respect to a second coordinate system. The controller 30 calculates/obtains and combines a plurality of transforms (T1-T5) from the various components of the system 10 to control the manipulator 14, as described below.

As shown in FIG. 3, the transforms include a first transform (T1) between the base 16 and the tool 20, a second transform (T2) between the tool 20 and the tool tracker 52, a third transform (T3) between the localizer 44 and the tool tracker 52, and a fourth transform (T4) between the localizer 44 and one or more of the patient trackers 54, 56. One exemplary system and method for obtaining the transforms of the various components of the system is explained in U.S.

Pat. No. 9,119,655, entitled, "Surgical Manipulator Capable of Controlling a Surgical Instrument in Multiple Modes," the disclosure of which is hereby incorporated by reference.

The output (e.g., values) of the transforms (T1)-(T4) are regarded as raw data when obtained instantaneously (in near real time) and when unfiltered. Such raw data may be understood as being derived from an instantaneous transform, i.e., an instantaneous determination of the state of one component of the system 10 relative to the state of another component. On the other hand, the output values of such transforms are regarded as filtered data when the values are filtered, such as for reasons described below.

To implement the aforementioned data fusion technique, the controller 30 acquires raw kinematic measurement data relating to a state of the tool 20. The state of the tool 20 may be determined relative to the manipulator coordinate system MNPL. In some instances, the raw kinematic measurement data may relate to the state of the tool 20 relative to the base 16. The state of the tool 20 is measured relative to the base 16 because the state of the base 16 is assumed to be stationary and the tool 20 moves relative to the base 16. The raw kinematic measurement data may be obtained from the manipulator controller 60. Specifically, as shown in FIG. 1, the controller 30 is configured to acquire the raw kinematic measurement data by acquiring one or more values of a first instantaneous transform (T1) between a state of the base 16 and the state of the tool 20. Here, the raw kinematic measurement data may be obtained from kinematic data of the manipulator 14. In particular, the controller 30 may acquire one or more values of the first instantaneous transform (T1) by applying a forward kinematic calculation to values acquired from the joint encoders 19. Thus, the state of the tool 20 can be determined relative to the manipulator coordinate system MNPL without intervention from the navigation system 32. In other words, the first instantaneous transform (T1) may be obtained irrespective of any measurements from the navigation system 32.

In FIG. 3, the first transform (T1) is indicated by an arrow having an origin at the base 16 and extending to and having an arrowhead pointing to the tool 20. In one exemplary convention used throughout FIG. 3, the arrowhead points to the component having its state derived or specified relative to the component at the origin. Those skilled in the art appreciate that the first transform (T1) may be inverted such that the raw kinematic measurement data represents the state of the base 16 relative to the state of the tool 20. Additionally, the first transform (T1) may be determined using any suitable reference frames (coordinate systems) on the base 16 and the tool 20.

The controller 30 may further acquire known relationship data relating to the state of the tool tracker 52 relative to the tool 20. In general, the known relationship data may be derived from any known relationship between the tool tracker 52 and the tool 20. In other words, the tool tracker 52 and the tool 20 have a relationship that is known or calculatable using any suitable method. The tool tracker 52 and the tool 20 may be fixed or moving relative to each other. For example, the tool tracker 52 may be attached directly to the tool 20, as shown in FIG. 3. Alternatively, the tool tracker 52 may be attached to one of the links 18, which move relative to the tool 20. In general, the tool tracker 52 and the tool 20 are tracked by different techniques, i.e., by navigation data and kinematic measurement data, respectively. The known relationship data assists to bridge the kinematic measurement data and the navigation data by aligning the tool tracker 52 and the tool 20 to a common coordinate system.

The known relationship data may be fixed (constant or static) or variable. In embodiments where the known relationship data is fixed, the known relationship data may be derived from calibration information relating to the tool tracker 52 and/or the tool 20. For example, the calibration information may be obtained at a manufacturing/assembly stage, e.g., using coordinate measuring machine (CMM) measurements, etc. The known relationship data may be obtained using any suitable method, such as reading the known relationship data from a computer-readable medium, an RFID tag, a barcode scanner, or the like. The known relationship data may be imported into system 10 at any suitable moment such that the known relationship data is readily accessible by the controller 30. In embodiments where the known relationship data is variable, the known relationship data may be measured or computed using any ancillary measurement system or components, such as additional sensors, trackers, encoders, or the like. The known relationship data may also be acquired after mounting the tool tracker 52 to the tool 20 in preparation for a procedure by using any suitable technique or calibration method.

Whether static or variable, the known relationship data may or may not be regarded as raw data, as described herein, depending on the desired technique for obtaining the same. In one embodiment, the controller 30 may acquire the known relationship data by acquiring one or more values of a second instantaneous transform (T2) between the state of the tool 20 and the state of the tool tracker 52. The second transform (T2) may be determined with respect to any suitable coordinate system or frame on the tool tracker 52 and the tool 20.

In other embodiments, the controller 30 may determine the second transform (T2) using any one or more of the kinematic measurement data from the manipulator 14 and navigation data from the navigation system 32 such that known relationship data is not utilized. For example, the second transform (T2) may be calculated using one or more of raw kinematic measurement data relating to the state of the tool 20 relative to the base 16 from the manipulator 14 and raw navigation data relating to the state of the tracker 52 relative to the localizer 44 from the navigation system 32. For example, the tool 20 may be rotated about its wrist to create a circular or spherical fit of the tool 20 relative to the tool tracker 52.

The controller 30 is further configured to acquire, from the navigation system 32, raw navigation data relating to the state of the tool tracker 52 relative to the localizer 44. The controller 30 may do so by acquiring one or more values of a third instantaneous transform (T3) between the tool tracker 52 and the localizer 44. The third transform (T3) can be calculated using navigation data alone, irrespective of kinematic measurement data from the manipulator 14. Here, the state of the localizer 44 is assumed stationary and the tool tracker 52 is assumed to move during operation. Thus, the tool tracker 52 is tracked relative to the localizer 44. The third transform (T3) is shown in FIG. 3 using an arrow originating at the localizer 44 and pointing towards the tool tracker 52. The direction of transform (T3) is opposite to transforms (T1) and (T2). Accordingly, transform (T3) should be inverted prior to combining (T3) with transforms (T1) and (T2). Consistent with the convention shown in FIG. 3, transform (T3) is hereinafter referenced as (T3') to indicate the inverted nature of this transform relative to the others in FIG. 3.

The fourth transform (T4) between the localizer 44 and one or more of the patient trackers 54, 56 may be determined by the controller 30 by similar techniques and assumptions as described above with respect to transform (T3). Specifically, the localizer 44 is configured to monitor the state of one or more of the patient trackers 54, 56 and the controller 30 is configured to acquire, from the navigation system 32, raw navigation data relating to the state of the one or more of the patient trackers 54, 56 relative to the localizer 44. The controller 30 acquires the raw navigation data by acquiring one or more values of the fourth instantaneous transform (T4) between the one or more of the patient trackers 54, 56 and the localizer 44.

As shown in FIG. 3, a fifth transform (T5) may be calculated between one or more of the patient trackers 54, 56 and the virtual boundary 55 associated with the anatomy of the patient 12 using registration techniques involving the navigation system 32 and the pointer (P). Specifically, the pointer (P) is tracked by the navigation system 32 via the pointer tracker (PT) and is touched to various points on a surface of the anatomy. The navigation system 32, knowing the state of the pointer (P), registers the state of the anatomy with respect to one or more of the patient trackers 54, 56. Alternatively, (T5) may be broken up into additional (intermediate) transforms that are combined to result in (T5). For example, the additional transforms may correspond to implant placement (surgical planning) relative to a pre-op image, acquired using techniques such as CT, MRI, etc., and location of the one or more patient trackers 54, 56 relative to that same pre-op image (registration). One exemplary system and method for registering the anatomy is explained in U.S. Pat. No. 9,119,655, entitled, "Surgical Manipulator Capable of Controlling a Surgical Instrument in Multiple Modes," the disclosure of which is hereby incorporated by reference.

Figure 4:
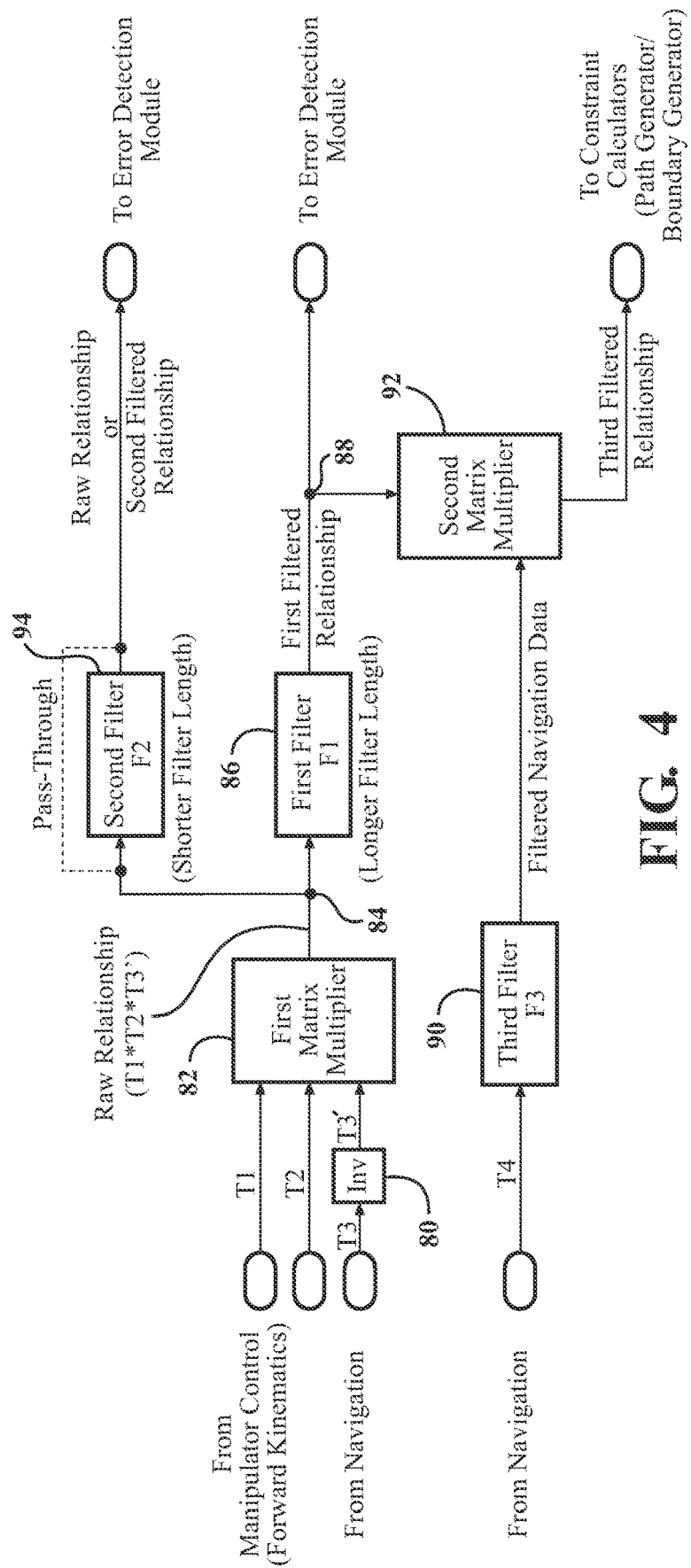
FIG. 4 is a block diagram of techniques, implemented by the controller, for fusing data from the manipulator and the navigation system to control the manipulator and for detecting error or loss of accuracy, according to one embodiment.

FIG. 4 is a block diagram illustrating, in part, aspects of the data fusion techniques implemented by the controller 30 and as described herein. As shown, transforms (T1)-(T4) are provided from their respective sources, as described above. The third transform (T3) is inputted into an inverse block 80 representing inverse matrix calculation as described above. Thus, the output of the inverse block 80 is the inverted third transform (T3'). Transform (T5) is omitted from FIG. 4 because transform (T5) is not directly utilized by the data fusion block, whose final output gives the pose of the one or more patient trackers 54, 56 with respect to the base 16. Instead, transform (T5) is utilized by downstream constraint generator blocks. Aspects of the data fusion calculations will be further described below.

The controller 30 is configured to combine the raw kinematic measurement data, the known relationship data and the raw navigation data to determine a raw relationship between the base 16 and the localizer 44. Specifically, the controller 30 combines values of each of the first, second, and third transforms (T1), (T2), (T3') to determine the raw relationship. As shown in FIG. 4, the controller 30 does so by applying a matrix multiplier at block 82. The matrix multiplier 82 receives the transforms (T1), (T2), and (T3') as inputs and performs matrix multiplication operations (including multiplication of matrices and concatenation of transforms) to combine transforms (T1), (T2), and (T3'). The output of the matrix multiplier 82 is the combination of transforms (T1), (T2), and (T3').

When transforms (T1), (T2), and (T3') are combined, the result is the raw relationship defining the state of the localizer 44 relative to the state of the base 16. Viewed with respect to FIG. 3, this raw relationship may be understood as the (instantaneous) spatial combination of the arrows of (T1), (T2), and (T3') originating at the base 16, extending to the tool 20, through the tool tracker 52, and terminating at the localizer 44.

Since the transforms (T1), (T2), and (T3') are generally raw data when inputted into the matrix multiplier 82, the output of the matrix multiplier 82 is consequently also raw data. In other words, the raw relationship may be understood as representing an actual and instantaneous state of the localizer 44 relative to the base 16. FIG. 4 includes a node 84 provided at the output of the matrix multiplier 82 representing for simplicity a point in the block diagram where the raw relationship is available. The raw relationship, which is based on pose data, is primarily or entirely a spatial relationship. However, the sequences of raw relationships may also signify one or more relationships that are derived from spatial parameters, such as relationships with respect to velocity and/or acceleration of the respective components used in calculating the raw relationship. As will be described, this raw relationship is used for more than one purpose.

Figure 5:
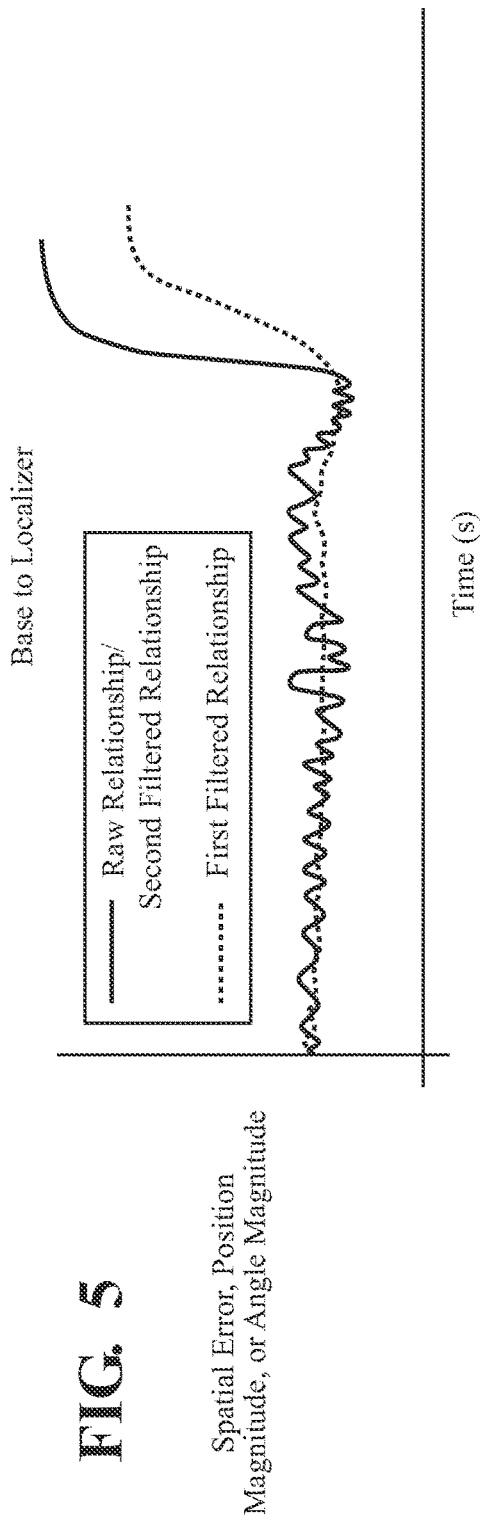
FIG. 5 is a diagram comparing signal of a first filtered transform and a raw transform (or second filtered transform) between a base of the manipulator and a localizer of the navigation system over time, according to one embodiment.

As shown in FIG. 5, the raw relationship can be represented as a signal (bold line) in the time-domain. The signal in FIG. 5 is a 6DOF pose such that the plot of FIG. 5 can be considered a plot of a single component (x, y, z, r, p, y) or as the magnitude of position or angle. The plot of FIG. 5 may be repeated for any one or more of these single components. As can be seen in FIG. 5, under normal operating conditions for the system 10, the raw relationship may exhibit variations resulting from minor changes in the relationship between the base 16 and the localizer 44. This variation can be due to physical movements and/or vibrations as well as due to measurement noise.

The raw relationship is particularly important, as will be described below, because both the base 16 and the localizer 44 are components of the system 10 that are assumed to be stationary and any appreciable variation in this transform may reveal system errors not previously detectable.

With the raw relationship now determined, the controller 30 is configured to filter the raw relationship. As shown in FIG. 4, the controller 30 is configured to input the raw relationship into a first filter shown at block 86. The first filter 86 is a digital temporal filter that filters the raw relationship in the time-domain. Filtering may be understood as performing a type of averaging over a time history of data. Filtering does not affect the update or measurement rate but rather the frequency of content of the output signal (e.g., how quickly or smoothly the output changes), yet still providing a new output for each sample. The first filter 86 results in latency in responding to either the base 16 and/or the localizer 44 moving. As will be described below, the first filter 86 may consequently result in spatial filtering by ultimately causing the manipulator 14 to lag (as compared with the raw relationship) in the spatial domain.

The first filtered relationship is available at node 88 in FIG. 4 at the output of the first filter 86. As will be described below, this first filtered relationship is involved in the calculation of constraints and downstream control commands, ultimately used to control the manipulator 14.

Filtering is performed on the raw relationship for two primary purposes, i.e., reducing noise and increasing system stability. If it were possible, using the raw data alone to control the system 10 would be preferred since doing so would give the fastest and most accurate response. However, filtering is needed because of practical limitations on the system 10. Such practical limitations include noise reduction and stability improvements by removal of positive feedback. The localizer 44 is capable of operating at a much higher bandwidth as compared to the manipulator 14. That is, the localizer 44 tracks poses of the trackers 52, 54, 56 faster than the manipulator 14 can respond. Controlling off the raw relationship alone causes instability of system 10 because the manipulator 14 must react to commanded movements including those arising from random signal variation (i.e., noise), which are provided at the rate of the localizer 44. For example, the manipulator 14 would have to respond to every variation in the raw relationship shown in FIG. 5. Commanded movement occurring at a rate higher than the manipulator 14 can respond, results in heat, audible noise, mechanical wear, and potentially resonance which can cause system instability. Because the localization data feedback represents an outer positioning loop, it is important to not close this outer loop at a higher bandwidth than the manipulator 14 can respond, to avoid instability.

Filtering reduces the bandwidth of the outer positioning loop thereby accommodating the bandwidth limitations of the inner positioning loop of the manipulator 14. Through such filtering, noise is reduced and stability is improved by removal or reduction in positive feedback. The manipulator 14 is prevented from reacting to every minor change in the raw relationship. Otherwise, if the manipulator 14 had to react to noisy data, the manipulator 14 may be susceptible to spatial overshoot of tool 20 along the tool path (such as when turning corners). Such spatial overshoot may cause the tool 20 to overcut the anatomy contrary to best design practices of favoring undercutting rather than overcutting. Instead, filtering of the raw relationship causes the manipulator 14 to behave more smoothly and run more efficiently. Further, noise may be introduced into the system 10 through measurement error in the sensors (e.g., encoders, localization feedback data, etc.). Filtering limits overall noise to a threshold tolerable by the system 10.

The first filter 86 filters the raw relationship according to a first filter length to produce a first filtered relationship between the base 16 and the localizer 44. In general, the greater the filter length for the filter, the greater the filter latency (delay) and averaging. In other words, a greater filter length provides more time to take into account (or average) determinations of the raw relationship over time. Thus, the greater the filter length, the more smooth the filtered relationship is over time. In other words, filtering affects the smoothness of the output, rather than the input.

In one embodiment, the first filter 86 may be understood as averaging inputted data, or averaging a time history of data. The first filter 86 may be one or more of various types of filters. For example, the first filter 86 may be an infinite impulse response (IIR) filter, a finite impulse response filter (FIR), a "boxcar" filter, a moving average filter, or the like. The filter length takes into account the time history of the filter. Examples of a filter length include a "time constant" for IIR filters, number of taps or coefficients (i.e., memory depth) for a FIR (finite impulse response) filter, or any parameter of a filter relating to the amount of depth of data that is processed or averaged. In addition, the filter order and length maybe chosen to meet requirements of the application. Generally, the filtering described herein applies to low pass-type filtering, however, other filter-types, such as band pass, high pass, or notch filtering may be utilized.

The filter length may be expressed as a unit of time. For example, the filter length may be represented in milliseconds (ms) or seconds (s). In one embodiment, the first filter length is greater than or equal to 100 ms and less than or equal to 1000 ms. For example, the first filter length may be 1000 ms. In this example, for any given time step, the filtered relationship is based on the raw relationship determinations averaged over the previous 1000 ms relative to the given time step.

In FIG. 5, the effect of filtering is demonstrated whereby the raw relationship is compared with its corresponding first filtered relationship. The first filtered relationship is illustrated as a signal provided directly over the signal of the raw relationship. The variations in the raw relationship signal are substantially reduced in the filtered relationship signal. In other words, the filtered relationship is a smoother version of the raw relationship. The smoothness of the filtered relationship depends on the value of the filter length. It is to be understood that FIG. 5 is provided for simplicity in explanation and that the signals of the raw relationship and the first filtered relationship may be substantially different than as shown and may exist over different durations of time from one another. Once again, the signal of the filtered relationship in FIG. 5 is a 6DOF pose such that the plot of FIG. 5 can be considered a plot of a single component (x, y, z, r, p, y) or as the magnitude of position or angle. The plot of FIG. 5 may be repeated for any one or more of these single components.

Referring back to FIG. 4, the controller 30 also filters the raw navigation data relating to the state of the one or more patient trackers 54, 56 relative to the localizer 44 to produce filtered navigation data. Specifically, the fourth transform (T4) is inputted into a third filter 90, which is a temporal filter, such as a moving average filter, similar to the first filter 86. The output of the third filter 90 is the filtered navigation data. The third filter 90 is utilized for many of the same reasons described above with respect to the first filter 86, i.e., signal noise reduction and increasing system stability. In this case, however, the third filter 90 is tuned based on the bandwidth of the patient anatomy rather than the manipulator 14. The third filter 90 helps dampen the response of the manipulator 14 in responding to self-induced anatomy (e.g., leg) motion due to tool forces. Without sufficient filtering, positive feedback and resulting instability can result from responding too aggressively to the self-induced leg motion.

The third filter 90 may also be represented as a filter length and may be any such filter length as those described herein for the first filter 86. In one embodiment, the filter length of the third filter 90 is greater than 10 ms and less than or equal to 100 ms. In one example, the filter length of the third filter 90 is 60 ms. The third filter 90 results in latency in responding to movement of the anatomy.

The filter length of the third filter 90 is generally less than the filter length for the first filter 86 for practical considerations. Mainly, the first filter 86 filters the raw relationship between two components of the system (i.e., the base 16 and the localizer 44) that are assumed to be stationary. Measurements of the tool tracker 52 play a role in an outer position loop used to adjust/correct commands to the manipulator 14. The length of the first filter 86 increases the time interval over which manipulator 14 positioning errors are corrected, a minimum amount of which is required to maintain stability To the contrary, the third filter 90 filters the raw navigation data including the state of the one or more patient trackers 54, 56, which are assumed to move during operation of the system 10. Movement of the patient trackers 54, 56 may result from movement of a table on which the patient 12 rests, movement of the patient 12 generally, and/or local movement of the anatomy subject to the procedure. Movement may also occur from anatomy holder dynamics, cut forces affecting movement of the anatomy, and/or physical force applied to the anatomy by an external source, i.e., another person, or a collision with an object. It is desirable to limit the length of the third filter 90, e.g., to allow the manipulator 14 to track/respond to motion within practical limits needed for stability.

The first filter 86 can afford applying a relatively longer filter length (slower response) to the raw relationship because this relationship is based on components assumed to be stationary. On the other hand, the third filter 90 requires a shorter filter length to allow fast response to movement of the one or more patient trackers 54, 56.

As shown in FIG. 4, the controller 30 combines the first filtered relationship (from the first filter 86) and the filtered navigation data (from the third filter 90) to produce a third filtered relationship. The controller 30 does so by utilizing a second matrix multiplier at block 92, which operates similar to the matrix multiplier at block 82. The third filtered relationship is a filtered relationship between the base 16 and one or more of the patient trackers 54, 56. The output of the second matrix multiplier 92 is the combination of (first) filtered transforms (T1)*(T2)*(T3'), and (third) filtered transform (T4). The combination of the filtered transforms (T1)*(T2)*(T3') provides a signal at the output of the first filter 86, which can be seen at node 88 in FIG. 4, for reference. Viewed with respect to FIG. 3, the third filtered relationship may be understood as the (filtered) spatial combination of the arrows of (T1), (T2), (T3'), and (T4) originating at the base 16, extending to the tool 20, through the tool tracker 52, to the localizer 44 and terminating at one or more of the patient trackers 54, 56.

The controller 30 is configured to utilize the third filtered relationship to generate the tool path and/or to position the virtual boundaries 55 relative to the patient anatomy and to convert the same into coordinates relative to the base 16 for controlling the manipulator 14. In FIG. 4, the output of the second matrix multiplier at block 92 is passed to the manipulator controller 60 such that the path generator 69 generates the tool path based on the third filtered relationship and such that the boundary generator 66 generates the virtual boundaries 55 based on the third filtered relationship.

III. System and Method for Detecting Errors and Loss of System Accuracy

Techniques have been described above for fusing the kinematic measurement data and navigation data and filtering the same to obtain the (intermediate) first filtered relationship, and ultimately, the (final) third filtered relationship for controlling the manipulator 14. Notably, the raw relationship between the base 16 and the localizer 44 remains available (at node 84 in FIG. 4) prior to being filtered by the first filter 86. This raw relationship is exploited for techniques described herein to detect errors and/or loss of accuracy in the system 10. Details regarding the theory and implementation of this error detection technique are provided below.

During typical operation of the system 10, there is an assumption that both the base 16 and the localizer 44 are stationary. Therefore, provided that neither the base 16 nor the localizer 44 moves during machining, digital filtering (as described above) can be performed on the raw relationship without directly affecting the dynamic response of the manipulator 14 to tracking of movement of the patient trackers 54, 56. However, there are downsides to this filtering. For example, if the base 16 and/or the localizer 44 do move during machining, then the first filtered relationship (base 16 to localizer 44), and ultimately, the third filtered relationship (base 16 to patient trackers 54, 56) become inaccurate and/or invalid. Furthermore, as described above, the first filter 86 generally has a longer filter length to accommodate stability requirements of the outer position loop. Extracting the raw relationship before filtering by the first filter 86 allows error determinations to be made instantaneously or near instantaneously that would otherwise be delayed by filtering.

Even though the assumption is that neither the manipulator 14 nor the localizer 44 is actively moving during machining, it is desirable to allow the raw relationship to adjust (via filtering) during runtime rather than simply performing a "one time" registration to compute a fixed transform. The outer positioning loop is enabled by allowing this raw relationship to adjust gradually during runtime. In other words, if the raw relationship were to be held constant, the outer positioning loop would not be active. Errors in the positioning of the manipulator 14, e.g., based on encoder data or calibration errors, are corrected by the system 10 by making fine adjustments to the raw relationship over time. In a sense, this can be thought of as the manipulator 14 positioning the localizer 44 (virtually) as needed relative to its base 16 so that the tool tracker 52 and the one or more patient trackers 54, 56 are in correct positions relative to each other. Said differently, if the first transform (T1) is not aligned with the third transform (T3), the manipulator 14 virtually adjusts the localizer 44 to be in the correct state to align the transforms (T1), (T3). The result is that the subsequent commands to the manipulator 14, converted from anatomy coordinates to base coordinates using this updated transform, cause the tool positioning to converge to a more accurate result, compared to if the localization data from the tool tracker 52 was not used.

From an accuracy standpoint, if all components in the system 10 were perfectly accurate, then the raw relationship would be a constant with no variation or noise. However, this is not the case, as shown by the raw relationship signal in FIG. 5. Variation in the raw relationship exists and may be correlated to errors or loss of accuracy in the system 10. As a positioning device, the manipulator 14 is designed to have very high repeatability and incremental accuracy (in a small/local working volume). However, the manipulator 14 may not be as accurate when measured over its entire workspace. On the other hand, the localizer 44 is designed to exhibit high and consistent accuracy over its entire workspace. As the manipulator 14 moves from one part of the workspace to another, there will be some (expected) positioning error as a result. This error is measured by the navigation system 32 through the localizer 44 and the tool tracker 52. As a result, the raw relationship of the transform between the base 16 and the localizer 44 updates. This update is expected to be small (approximately 1 mm or less), within the range of the global positioning accuracy of the manipulator 14. These updates are reflected by the oscillations in the raw relationship signal in FIG. 5.

A variation of the raw relationship over time gives an indication of the overall positioning error in the system 10 from a perspective of the localizer 44. The raw relationship is expected to see small and gradual changes over time based on calibration or other positioning errors in the system 10, as shown in FIG. 5. However, any abrupt or significant magnitude changes in the raw relationship indicate a notable issue in the system 10. One example of such abrupt change in the raw relationship is shown in its signal in FIG. 5 wherein the magnitude of the signal exhibits a spike, which can be seen instantaneously in the raw relationship and delayed in the first filtered relationship. To detect a loss in accuracy of the system 10, the error detection technique is provided to compare the values of the raw relationship (or a lightly filtered version of the raw relationship) with the values of the first filtered relationship, which is more heavily filtered.

To implement this error detection technique, the controller 30, as shown in FIG. 4, is configured, according to one embodiment, to filter the raw relationship by applying the raw relationship to a second filter 94. The second filter 94 has a (second) filter length being shorter than the first filter length of the first filter 86. That is, the raw relationship is lightly filtered relative to the filtering of the first filtered relationship. The output of the second filter 94 is a second filtered relationship between the base 16 and the localizer 44. The second filtered relationship is generated specifically for the error detection technique. In one example, the filter length of the second filter 94 is greater than 0 ms and less than or equal to 50 ms, as compared to, for example, the filter length of 1000 ms for the first filter 86.

In this embodiment, the raw relationship is filtered by the second filter 94 to remove high frequency noise or high frequency jitter from the raw relationship signal, and to help isolate from false trips on the error detection. The amount of filtering (filter length) applied to the raw relationship for error detection purposes should be chosen, such that, it is long enough to remove the aforementioned high frequency noise/jitter in the signal, but short enough such that error detection reacts quickly enough to prevent significant errors in machining due to loss of accuracy in the system 10. When filtered, it is generally understood that the filter length is greater than zero. In one preferred embodiment, the error detection technique filters the raw relationship by a filter length allowing detection of errors in a time interval similar to the filter length of the closed loop positioning of the system 10. In this embodiment, the controller 30 compares the first filtered relationship to the second filtered relationship to determine whether an error has occurred relating to at least one of the manipulator 14 and the localizer 44.

In another embodiment, the controller 30, as shown in FIG. 4, is configured to compare the raw relationship (instead of the second filtered relationship) to the first filtered relationship to determine whether the error has occurred. In this example, the raw relationship is not filtered. Hypothetically, it may also be understood that the raw relationship, in this embodiment, is filtered by the second filter 94 having a filter length of zero. If filtered by filter length of zero, the raw relationship "passes through" the second filter 94. Whether unfiltered, or filtered by filter length of zero, the raw relationship is the same in both of these instances. In this embodiment, the controller 30 compares the raw relationship to the first filtered relationship to determine whether the error has occurred relating to at least one of the manipulator 14 and the localizer 44.

The controller 30 is configured to make this comparison by accessing each of the first filtered relationship and the raw relationship/second filtered relationship. The first filtered relationship, as shown in FIG. 4, remains available at node 88 before being inputted into the second matrix multiplier 92 for controlling the manipulator 14. The first filtered relationship is duplicated or accessed at this point 88 for error detection purposes, leaving the first filtered relationship intact for control purposes downstream. The raw relationship or second filtered relationship are accessible from the branch in FIG. 4 stemming from node 84 and comprising the second filter 94, if utilized.

Each of the first filtered relationship and the raw relationship/second filtered relationship are then passed to the error detection module 96. The error detection module may be implemented by the manipulator controller 60, as shown in FIG. 2. The error detection module 96 may comprise any suitable computer-executable instructions, algorithms, and/or logic for comparing the raw relationship or second filtered relationship to the first filtered relationship. In one embodiment, the error detection module 96 compares the raw relationship or second filtered relationship to the first filtered relationship by determining a difference between the same.

In general, the first filtered relationship alone may not be suitable for error handling. Mainly, the filter length of the first filter 86 may be too long for real time error detection. In other words, the system 10 would not be able to react to detection of the error quickly enough if the first filtered relationship alone is utilized. As part of this error handling method, the first filtered relationship is utilized instead as a 'steady state' or mean value of the raw relationship/second filtered relationship. By subtracting the first filtered relationship from the raw relationship/second filtered relationship, the signal is de-trended (i.e., its mean value updated over time by the first filter 86 is removed) such that the variation may be more easily evaluated. The resulting difference represents variation or changes in the raw relationship over time. In turn, the amount of variation between the first filtered relationship and the raw relationship/second filtered relationship gives an indicator of degradation in runtime system accuracy.

Figure 6:
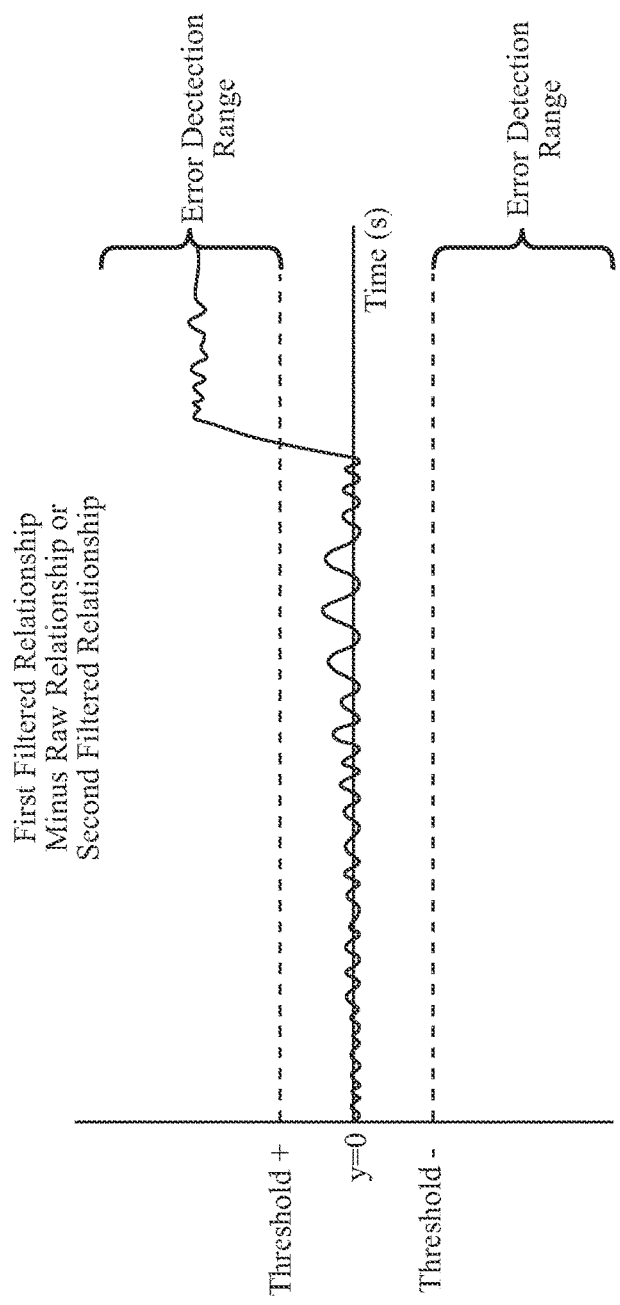
FIG. 6 is a diagram of a signal representing variation over time between the transforms of FIG. 5 wherein the variation is compared with a predetermined threshold for determining whether an error or loss of accuracy has occurred, according to one embodiment.

In one embodiment, comparing the first filtered relationship to the raw relationship/second filtered relationship occurs by converting each relationship to its respective positional (xyz) and angular components and by subtracting the respective components of each relationship. After subtraction, the magnitude of the positional and angular components may be computed, respectively, and each compared to a corresponding positional/angular predetermined threshold, as shown in FIG. 6. Thus, the result of this comparison is shown in FIG. 6.

The signal in FIG. 6 is a function of the separation between the first filtered relationship and the raw relationship/second filtered relationship. In FIG. 6, the relationships are shown according to any one or more of component of the spatial error (x, y, z, r, p, y), the position magnitude, or the angle magnitude, with respect to time. That is, the greater the separation between these transforms in FIG. 5, the greater the magnitude of variation in FIG. 6. This variation is compared to the predetermined threshold, as shown in FIG. 6. If the variation exceeds the threshold, a loss in accuracy of the system 10 is determined. In FIG. 6, the threshold is indicated by a sample upper threshold (+) that also represents the floor of an error detection range. In FIG. 5, an abrupt change in the raw relationship/second filtered relationship occurs with respect to the first filtered relationship. In turn, this abrupt change causes, at the same time step, a corresponding large separation between the transforms in FIG. 6. When the variation signal in FIG. 6 exceeds the threshold and enters the error detection range, the error in the system 10 is detected.

Preferably, the threshold should be greater than zero such that minor/negligible variations between the transforms do not trigger errors. Instead, the sensitivity of the threshold should be set such that only noticeable and/or meaningful errors of the system 10 exceed the threshold. The threshold for the positional and/or angular errors may be chosen based on a predetermined error budget of the system 10. For example, if the system 10 is designed to have a total error of less than 0.5 mm, the positional threshold may be set at 1.0 mm such that there is some safety margin to avoid false trips, but enough sensitivity to detect subtle degradations in performance. The threshold may be a position threshold, an angle (orientation) threshold, or any combination thereof. The threshold may be an upper threshold or a lower threshold and may have other configurations other than that shown in FIG. 6.

In an alternative embodiment, the error can be detected by evaluating either of the raw relationship or second filtered relationship (alone) for variations, without comparing the same to the first filtered relationship. Mainly, comparing (or subtracting) the first filtered relationship and the raw relationship/second filtered relationship is done for convenience so that the result can be compared to the predetermined threshold. Using either of the raw relationship/second filtered relationship alone would require detecting changes in a present value relative to past values. On the other hand, comparing the first filtered relationship and the raw relationship/second filtered relationship (as described above) allows simple comparison to the predetermined threshold rather than the analysis needed to detect the aforementioned changes of the present value relative to past values. When utilizing the raw relationship alone, detection of such changes can be done using a high pass filter and looking for a signal above the predetermined threshold on the output. When utilizing the second filtered relationship alone, which is a low-pass filter, detection of such changes can also be done using a high pass filter to detect abrupt change. This technique is equivalent to passing of the raw relationship into a band pass filter and performing comparison of the output to the predetermined threshold. To reiterate, using the signal from the first filtered relationship, which is used for control purposes, alone is not suitable to detect the aforementioned error. Those skilled in the art appreciate that there are other mathematically equivalent techniques to detect the error other than those described specifically herein.

In any of the aforementioned embodiments, the detected error generally indicates the error in the system 10 or a loss in accuracy of the system 10. Because the error detection technique compares relationships between the base 16 and the localizer 44, the error generally relates to at least one of the manipulator 14 and the localizer 44.

Specific examples of the error as it relates to the manipulator 14 include, but are not limited to, the following: undesired movement of the base 16 (such as during machining); improper operation of the manipulator 14; failure of any one or more components of the manipulator 14 such as damage to one or more of the links 18 and/or increase in gear box compliance at any one or more of the joints (J1-J6); improper kinematic calibration of the manipulator 14; failure or errors in the encoders (e.g., slippage, noise, nonlinearity, misalignment); and any other electrical or mechanical degradation of the same.

Specific examples of the error as it relates to the localizer 44 include, but are not limited to, the following: undesired movement of the localizer 44 (such as during machining); improper operation of the localizer 44; failure of any one or more components of the localizer 44; improper calibration of the localizer 44; and any other electrical or mechanical degradation of the same. Additionally, the error may indicate improper calibration of the tool 20. The error may relate to any one or more of the aforementioned problems. The error may relate to other problems associated with any other component or subcomponent not specifically recited herein and being in the path of transforms (T1), (T2), and (T3').

Because the techniques described herein use the combination of data from the manipulator 14 and the localizer 44, the techniques are able to detect failures not able to be detected in either component standalone. In this manner, the error detection techniques provide a check of the full system. This helps avoid a single source of failure, a critical design aspect for a safety-critical system, such as surgical robotics. The techniques also enable detection of a stack up problem, in which the aggregate error (based upon multiple subtle errors adding up) exceeds an acceptable limit.

The controller 30 is configured to modify operation of the system 10 and/or manipulator 14 in response to determining that the error has occurred. This may be done so to prevent damage to the patient 12 and/or the system 10 as a result of operation of the manipulator 14 during the error. The controller 30 may do so using any suitable technique, such as commanding the manipulator 14 to hold position, power off, lock a current state of the manipulator 14, and the like. Additionally, or alternatively, the controller 30 may power off the tool 20 or energy applicator 24 by, for example, stopping burr rotation, saw actuation, and/or application of ultrasonic energy thereto, and the like. Those skilled in the art appreciate that controller 30 may modify operation of the system 10 and/or manipulator 10 according to other techniques not described herein in response to determining that the error has occurred.

In response to detection of the error, the controller 30 may command prompt of an alert or notification 102 on any one or more of the displays 38 of the system 10, as shown on the display in FIG. 1, for example. The alert or notification 102 relates to occurrence of the error to inform operator(s) of the system 10 that the error, detected according to the aforementioned techniques, has occurred. The alert or notification 102 may be audible, visual, haptic or any combination of the same. In other embodiments, the alert or notification 102 may be implemented using any other component of the system 10, such as the manipulator 14, the manipulator cart 17, the navigation system 32, or the like.

The aforementioned error detection method provides a bona fide means for detecting whether a loss in accuracy or an error has occurred in the system 10. In general, the error detection technique may do so without precisely identifying what the error is or where in the system 10 the error occurred. From a real time control standpoint, the precise cause of the error is not critical if the controller 30 ultimately halts the system or manipulator 14 and informs the operator(s). In other words, adverse consequences of the error are mitigated by immediately halting the system or manipulator 14. However, there may be practical reasons for determining the precise cause of the error. For example, such reasons may be related to improving service and diagnostics capabilities, improving GUI feedback to the user to assess the failure, and the like.

In such instances, the aforementioned error detection technique may be combined with auxiliary sensors to provide further specificity as to the cause of the error. Examples of such auxiliary sensors include, but are not limited to, sensors (such as secondary joint encoders, accelerometers, inertial sensors, velocity sensors, position sensors, etc.) in the localizer 44 and/or the manipulator 14, sensors in any one or more of the carts 17, 34 to detect brake release, auxiliary position sensing (e.g., lower bandwidth type), or the like. For example, one or more auxiliary sensors in the localizer 44 and/or the manipulator 14 may be configured to detect abrupt changes for the respective component. The controller 30 may determine whether the error occurred from the localizer 44 and/or the manipulator 14 by analyzing these measurements in conjunction with other measurements. Similar techniques may be applied to any other components of the system 10.

These auxiliary measurements may be used to directly detect common (expected) failure modes, and/or rule out causes of failure, allowing process of elimination to point to alternate causes. Additionally, if auxiliary sensors from more than one component detect an abrupt change, the controller 30 may compare/combine these measurements, and for example, apply weighting factors to the measurements to identify which component produced the error and by how much each component contributed to the error, as a whole. In other cases, the error may be tripped due to user action, e.g., moving the localizer 44 while machining. In such cases, the auxiliary sensors can be used to detect this error and give better guidance to the user to avoid future errors.

Such auxiliary sensors may provide measurements that can be detected and analyzed by the controller 30 and evaluated with respect to the detected error to determine the cause of the error. The level of specificity as to determining the cause of the error may depend on the particularity, quantity, location of the auxiliary sensors. In some embodiments, the auxiliary sensors may be used to rule out common errors or user actions (rather than component failures) in the system 10, such as undesired movement of the base 16 of the manipulator 14 and/or localizer 44, and the like.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical system comprising:
   a surgical tool;
   a manipulator comprising a base and a plurality of links and being configured to support the surgical tool;
   a navigation system comprising a tracker and a localizer being configured to monitor a state of the tracker; and
   one or more controllers coupled to the manipulator and the navigation system and being configured to:
      determine values of a first transform between a state of the base of the manipulator and a state of one or both of the localizer and the tracker of the navigation system;
      determine values of a second transform between the state of the localizer and the state of the tracker; and
      combine values of the first transform and the second transform to determine whether an error has occurred relating to one or both of the manipulator and the localizer.

2. The surgical system of claim 1, wherein the one or more controllers are configured to determine a relationship between the manipulator and the localizer based on the combined values of the first transform and second transform.

3. The surgical system of claim 2, wherein the one or more controllers are configured to utilize the relationship by being configured to compare present values of the relationship relative to past values of the relationship to determine whether the error has occurred.

4. The surgical system of claim 1, wherein the tracker is coupled to:
   the surgical tool;
   the base of the manipulator; or
   one or more of the links of the manipulator.

5. The surgical system of claim 1, wherein the tracker is an inertial tracker.

6. The surgical system of claim 1, wherein the one or more controllers are configured to modify operation of one or both of the manipulator and the surgical tool in response to determining that the error has occurred.

7. The surgical system of claim 1, wherein the one or more controllers are configured to generate an alert or notification relating to occurrence of the error.

8. The surgical system of claim 1, further comprising one or more auxiliary sensors coupled to one or both of the manipulator and the localizer and wherein the one or more controllers are further configured to analyze measurements from the one or more auxiliary sensors to determine a cause of the error.

9. The surgical system of claim 1, wherein the error is defined as one or more of:
   undesired movement of the manipulator;
   undesired movement of the localizer;
   failure of any one or more components of the manipulator or the localizer; and
   improper calibration data.

10. The surgical system of claim 1, wherein the one or more controllers determine values of the first transform by being configured to:
    acquire, from the manipulator, raw kinematic measurement data relating to a state of the surgical tool relative to the base; and
    acquire known relationship data relating to the state of the tracker relative to the surgical tool.

11. The surgical system of claim 10, wherein the one or more controllers determine values of the second transform by being configured to:
    acquire, from the navigation system, raw navigation data relating to the state of the tracker relative to the localizer.

12. The surgical system of claim 11, wherein the one or more controllers combine values of the first transform and the second transform by being configured to:
    combine the raw kinematic measurement data, the known relationship data, and the raw navigation data to determine a raw relationship between the base and the localizer.

13. The surgical system of claim 12, wherein the one or more controllers are configured to:
    filter the raw relationship according to a first filter length to produce a first filtered relationship between the base and the localizer for controlling the manipulator;
    filter the raw relationship according to a second filter length being shorter than the first filter length to produce a second filtered relationship between the base and the localizer; and
    utilize the second filtered relationship to determine whether the error has occurred.

14. A method of operating a surgical system, the surgical system comprising a surgical tool, a manipulator comprising a base and a plurality of links and being configured to support the surgical tool, a navigation system comprising a tracker and a localizer being configured to monitor a state of the tracker, one or more controllers coupled to the manipulator and the navigation system, the method comprising the one or more controllers performing the following:

determining values of a first transform between a state of the base of the manipulator and a state of one or both of the localizer and the tracker of the navigation system;

determining values of a second transform between the state of the localizer and the state of the tracker;

combining values of the first transform and the second transform for determining whether an error has occurred relating to one or both of the manipulator and the localizer, wherein the error is defined as one or more of:
- undesired movement of the manipulator;
- undesired movement of the localizer;
- failure of any one or more components of the manipulator or the localizer; and
- improper calibration data.

15. The method of claim 14, comprising the one or more controllers:
- determining a relationship between the manipulator and the localizer based on the combined values of the first transform and second transform; and
- utilizing the relationship for comparing present values of the relationship relative to past values of the relationship for determining whether the error has occurred.

16. The method of claim 14, comprising the one or more controllers modifying operation of one or both of the manipulator and the surgical tool in response to determining that the error has occurred.

17. The method of claim 14, comprising the one or more controllers generating an alert or notification relating to occurrence of the error.

18. The method of claim 14, comprising:
determining values of the first transform by the one or more controllers:
- acquiring, from the manipulator, raw kinematic measurement data relating to a state of the surgical tool relative to the base; and
- acquiring known relationship data relating to the state of the tracker relative to the surgical tool; and determining values of the second transform by the one or more controllers:
- acquiring, from the navigation system, raw navigation data relating to the state of the tracker relative to the localizer.

19. The method of claim 18, wherein combining values of the first transform and the second transform comprises the one or more controllers:
- combining the raw kinematic measurement data, the known relationship data, and the raw navigation data for determining a raw relationship between the base and the localizer.

20. The method of claim 19, comprising the one or more controllers:
- filtering the raw relationship according to a first filter length for producing a first filtered relationship between the base and the localizer for controlling the manipulator;
- filtering the raw relationship according to a second filter length being shorter than the first filter length for producing a second filtered relationship between the base and the localizer; and
- utilizing the second filtered relationship for determining whether the error has occurred.

* * * * *